United States Patent [19]
Seitz et al.

[11] Patent Number: 4,762,799
[45] Date of Patent: Aug. 9, 1988

[54] METHOD AND DEVICE FOR FLUORESCENCE DETERMINATION OF ALKALI METAL CATIONS

[75] Inventors: William R. Seitz, Durham, N.H.; Zhang Zhujun, Sian Shaansi, China; Jerome Mullin, Newmarket, N.H.

[73] Assignee: Fisher Scientific Company, Pittsburgh, Pa.

[21] Appl. No.: 775,563

[22] Filed: Sep. 13, 1985

[51] Int. Cl.$^4$ ............... G01N 21/77; G01N 33/20
[52] U.S. Cl. ................................. 436/79; 422/58; 422/68; 436/74; 436/172
[58] Field of Search .................. 436/79, 172, 74; 422/68, 58

[56] References Cited

U.S. PATENT DOCUMENTS

| | | | |
|---|---|---|---|
| 4,256,834 | 3/1981 | Zuk et al. | 436/800 |
| 4,272,485 | 6/1981 | Lübbers | 472/58 |
| 4,548,907 | 10/1985 | Seitz et al. | 436/172 |
| 4,552,697 | 11/1985 | Yip et al. | 260/396 N |
| 4,649,123 | 3/1987 | Charlton et al. | 436/74 |

OTHER PUBLICATIONS

Freeman et al., *Anal. Chem.* vol. 50, No. 9; Aug. 1978 pp.:1242-1246.

*Primary Examiner*—Barry S. Richman
*Assistant Examiner*—Robert J. Hill, Jr.
*Attorney, Agent, or Firm*—Alan M. Doernberg

[57] ABSTRACT

The concentration of a selected alkali metal cation in an aqueous sample is determined using an aqueous fill solution containing a dissolved polymeric cationic material (e.g., copper—PEI) and a dissolved fluorescent anionic material (e.g., ANS) and, in contact with the fill solution, an ionophore selective for the selected alkali metal cation. The aqueous fill solution is contacted with an aqueous sample through a membrane, the membrane being permeable to alkali metal cations, but impermeable to the polymeric cationic material. Fluorescence is detected either from molecules of fluorescent anionic material which have migrated from adjacent to the polymeric cationic material to adjacent to ionophore-complexed alkali metal cations or from molecules of fluorescent anionic material which have remained adjacent to the polymeric cationic material, or from both, especially through a fiber optic.

26 Claims, 1 Drawing Sheet

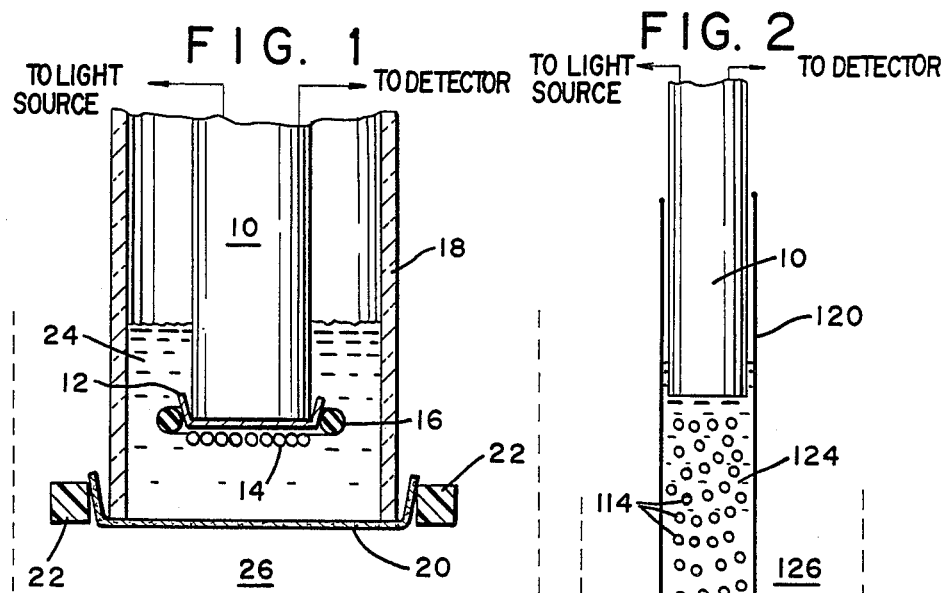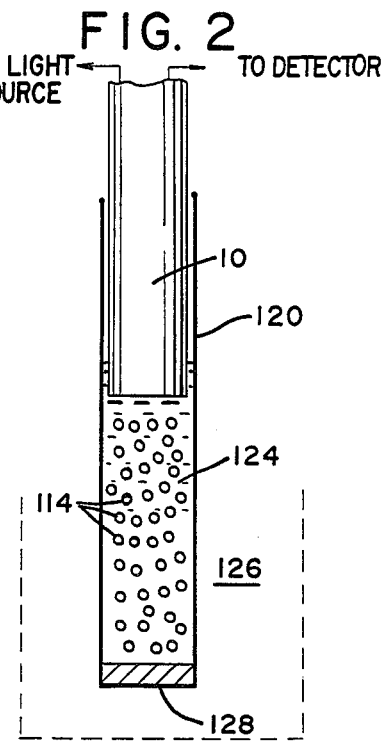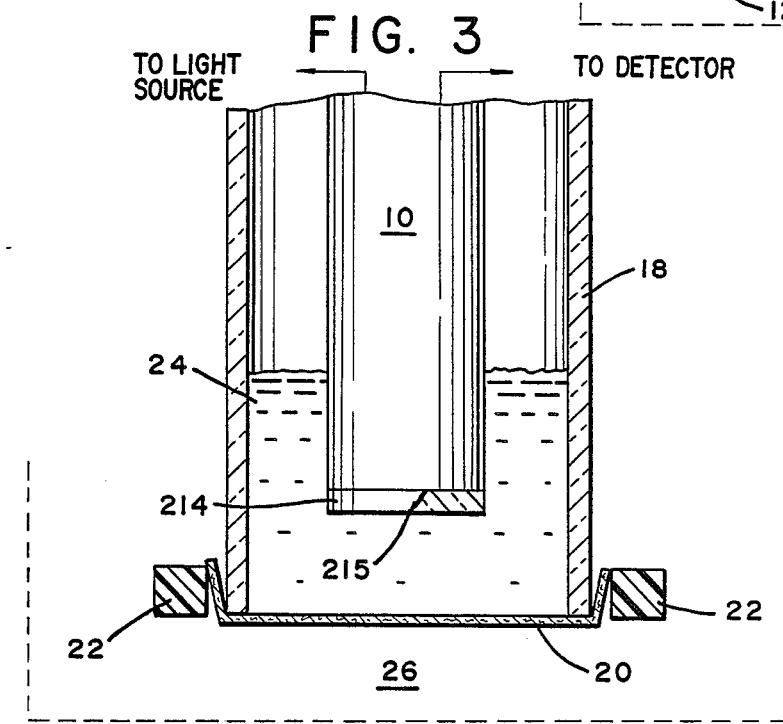

METHOD AND DEVICE FOR FLUORESCENCE DETERMINATION OF ALKALI METAL CATIONS

BACKGROUND OF THE INVENTION

The present invention relates to methods and devices for the determination of the concentration of one or more alkali metal cations in aqueous liquids, such as serum, based upon detection of fluoresence.

Alkali metal cation concentrations are normally determined by ion selective electrodes, in which an ionophore membrane selective for the cation (e.g., valinomycin for potassium detection) coats an electrode equipped for potentiometric measurement. Various materials, including crown ether compounds, have been suggested for use in such devices.

The Ames Division of Miles Laboratories, Inc. has proposed dry chemistry tests for $K^+$ involving a nonpolar membrane phase containing the ionophore valinomycin and either dye comigration into the membrane or dye deprotonation within the membrane. Clinical Chemistry, vol. 30, no. 6, p. 962, abstract 112 (1984). In either case the dye amount is determined by absorbance.

Fluorescence measurements of biological samples are sometimes made with devices employing fiber optics to convey light from the sample to a detector and/or to convey excitation light to the sample. Such devices are not used in the determination of alkali metal cations. Copending application U.S. Ser. No. 531,957 of Seitz, filed Sept. 14, 1983, describes the use of such a device in the determination of pH, employing dyes fluorescent in both protonated and deprotonated states. In Anal. Chem., vol. 54, pp. 821–823 (1982), L. Saari and W. R. Seitz describe a pH sensor based on immobilized fluoresceinamine.

BRIEF DESCRIPTION OF THE INVENTION

The present invention is based upon migration of fluorescent anionic materials in an aqueous fill solution from a dissolved cationic polymeric material to an ionophore/alkali metal cation complex, with a resultant wavelength shift or emergence of fluorescence. Accordingly, the present invention provides a method for determining the concentration of a selected alkali metal cation in an aqueous sample which comprises the steps:

(a) providing an aqueous fill solution containing a dissolved polymeric cationic material and a dissolved fluorescent anionic material;

(b) providing in contact with the fill solution an ionophore selective for the selected alkali metal cation;

(c) contacting the aqueous fill solution with an aqueous sample through a membrane, the membrane being permeable to alkali metal cations, but impermeable to the polymeric cationic material; and (d) detecting fluorescence either from molecules of fluorescent anionic material which have migrated from adjacent to the polymeric cationic material to adjacent to ionophore-complexed alkali metal cations or from molecules of fluorescent anionic material which have remained adjacent to the polymeric cationic material.

The present invention further provides a device for determining the concentration of a selected alkali metal cation in an aqueous sample, which device comprises:

(a) an aqueous fill solution containing a dissolved polymeric cationic material and a dissolved fluorescent anionic material, (b) an ionophore selective for the selected alkali metal cation in contact with the aqueous film solution;

(c) membrane means for permitting cations to migrate from a sample to the aqueous fill solution and for preventing the dissolved polymeric material from migrating out of the aqueous fill solution;

(d) excitation means for exciting the fluorescent anionic material; and (e) detection means for detecting fluorescence either from molecules of fluorescent anionic material which have migrated from adjacent to the polymeric cationic material to adjacent to ionophore-complexed alkali metal cations, or from molecules of fluorescent anionic material which have remained adjacent to the polymeric cationic material, or from both.

BRIEF DESCRIPTION OF THE DRAWINGS

FIG. 1 is an elevational view of the fill compartment and surrounding structure according to a first embodiment of the invention.

FIG. 2 is a view, similar to FIG. 1, according to a second embodiment.

FIG. 3 is a view, similar to FIG. 1, according to a third embodiment.

DETAILED DESCRIPTION OF THE INVENTION

The present invention provides a method and a device for determining the concentration of a selected alkali metal cation (e.g., $Na^+$, $K^+$ or $Li^+$) in an aqueous sample such as human serum, plasma, whole blood or urine. The several components used in both the method and device are described first: (1) the ionophore and (2) the aqueous fill solution containing (a) a dissolved polymeric material and (b) the anionic fluorophore. The ionophore provides the selectivity of the method or device: i.e., a potassium-selective ionophore such as valinomycin provides selectivity for $K^+$. It is, nevertheless, the interaction between the ionophore, the analyte cation, the anionic fluorophore and dissolved polymeric cationic material that enables the determination of alkali metal cations optically.

The ionophore used in the present invention can be any neutral or anionic material or substance, of low molecular weight or polymeric, that has a high binding efficiency for the selected alkali metal cations. Suitable materials are well-known in the art of ion-selective electrodes, and include crown-ether structures, other neutral carriers and ion exchangers. The ionophore, especially for detecting $K^+$ or $Li^+$, should preferably have a high selectivity for binding such selected alkali metal cation, even in the presence of large excesses of other alkali metal cations, and especially $Na^+$. When the selected alkali metal cation is $K^+$, then the ionophore employed preferably has a selectivity for $K^+$ over $Na^+$ of at most about $10^{-3}$, more preferably at most about $2 \times 10^{-4}$. Selectivity, in this context, means the ratio of the two ion concentrations which yield separately the same signal (i.e., bound cation amount) under otherwise identical conditions. Thus $k_{NaK} = 10^{-3}$ means that a given amount of cations are complexed when sodium is at one concentration (e.g., $10^{-1}$ molar) or when potassium is at one-thousandth such concentration (e.g., $10^{-4}$ molar). See A. Covington, Ion Selective Electrode Methodology, vol. I, pp. 15–18 (CRC Press 1979) and G. A. Rechnitz et al., Anal. Chem., vol. 38, p. 973 (1966). Of the materials used in the present Example 9, valinomycin has such a selectivity of approximately $10^{-4}$; polycrown DB 18-6 has such a selectivity of approximately $10^{-3}$.

As indicated below, the ionophore is in contact with the aqueous fill solution. While such contact can be made by dissolving or suspending certain ionophores in the aqueous fill solution, or dissolving certain ionophores in an organic liquid phase (including an organic liquid membrane phase) in contact with the aqueous fill solution, it is preferred to immobilize the ionophore in or on a solid phase in contact with the aqueous fill solution. Such immobilization may involve adsorption on beads (as in the Examples) or covalent or other attachment, or may involve forming a polymeric solid phase with the ionophore moiety attached or included.

In most forms of the present invention, it is desirable both for the aqueous liquid in immediate proximity to the ionophore to be accessible to excitation light and for fluorescence from such proximate aqueous liquid to be accessible to the detector. Accordingly, the solid phase may either be transparent to such excitation and fluorescent light (because of materials used or relative thinness) or positioned spatially so as not to block such light.

The cationic polymeric material (CPM) used in the method and device of the present invention has one necessary function and three preferred functions. The necessary function is to complex with (in an ion pairing sense) such molecules of anionic fluorescent material (AFM) as are not ion-paired with ionophore-alkali metal cation complexes. For this purpose, in the absence of any selected alkali metal cations, most and, preferably substantially all, of the AFM molecules are present in the aqueous fill solutions as such CPM/AFM ion pairs. The first preferred function of the CPM is to modify (by quenching or shifting) the fluorescence of the AFM in such CPM/AFM complex compared to the fluorescence of AFM molecules free in solution or ion-paired with alkali metal cation/ionophore complexes. For example, the copper-PEI complexes used in many of the Examples as the CPM strongly quenches the fluorescence of many (but not all) of the AFM molecules used.

The second preferred function of the CPM is to increase potentially the concentration of the AFM in the aqueous fill solution relative to the solubility limits of the AFM alone in water or in aqueous solutions of physiological pH and ionic strength. For example, the fluorescent anionic material can be substantially water-insoluble when it is not complexed, but solubilized in the aqueous fill solution by being complexed with the polymeric cationic material. In this case, the concentration of the fluorescent anionic material in the fill solution can be in excess of the solubility limits of the fluorescent anionic material in water when it is not complexed.

The third preferred function of the CPM is to entrap the AFM in the aqueous fill solution in those devices wherein the aqueous fill solution is separated from a sample chamber or space by a dialysis membrane or similar ion permeable structure. Such function permits the use of low molecular weight AFM molecules that would, in the absence of CPM, bleed out of the aqueous fill solution through the dialysis membrane. AFM molecules that are ion-paired with CPM (or as described below, with ionophore/alkali metal cation complexes) are, in general, in structure too large to migrate through such dialysis membranes. Accordingly, the loss of AFM through the dialysis membrane should be greatly reduced, even over a large number of sample measurements. Nevertheless, even with the optimal combination of CPM, AFM and dialysis membrane, it is expected that periodic replacement of the aqueous fill solution will occur.

A preferred class of CPM materials are those containing a carbon-nitrogen-hydrogen polymer and especially polyethyleneimine. The polymer may itself be cationic under the conditions of pH and ion strength of the aqueous fill solution, but, in some preferred forms, the polymer has a transition metal cation strongly bound thereto. Exemplary transition metal cations which can be bound to the carbon-nitrogen-hydrogen polymer (and especially to PEI) are those of the first row in Groups VIIIA and IB of Periodic Table, with nickel and copper being preferred and copper (especially in the divalent state) being most preferred. In other preferred forms, the polymer has bound thereto (in a relatively irreversible fashion) a cationic dye such as rhodamine. The cationic dye forms ion pairs with the anionic dye (e.g., AFM). If the optical properties of the two dyes are properly matched, then excitation energy is transferred from the anionic dye to the cationic dye, causing fluorescence of the cationic dye at a wavelength longer than, and thus distinguishable from, the fluorescence of the anionic dye.

Suitable anionic fluorescent materials (AFM) include fluors of the aromatic sulfonate, aromatic carboxylate, fluorescein and rhodamine families such as 8,1-ANS and Eosin Y [see for a general discussion of the structure and properties of such flours: Molecular Probes Catalog (R. Haughland 1985); G. G., Guilbault, *Practical Fluroescence Theory, Methods and Techniques* (M. Dekker 1973); C. A. Parker, *Photoluminescence of Solutions* (Elsevier 1968)]. Preferred AFMs will differ for particular CPMs used; generally, however, Eosin Y and 8,1-ANS are preferred for use with PEI-transition metal complexes and especially with PEI/Cu (II).

The aqueous filling solution may contain other constituents beyond the CPM, the AFM and water. Buffers or buffer systems may be used to hold the pH of the filling solution within a desired range; preferably, however, the buffer or buffer system is free of alkali metal cations, and more preferably is free of all metallic cations. Thus buffers based upon ammonium, quaternary ammonium or other nitrogenous cations are often used: e.g., tris(hydroxymethyl)aminomethane (commonly called Tris) in combination with HCl or other acids to achieve the desired pH. If the system is insensitive to a particular cation, e.g., $Li^+$, then such cation may be used as a part of the buffer system (as in certain Examples, below). Other optional components of the aqueous fill solution include ionic strength adjusters.

In the device of the present invention, the aqueous fill solution is preferably of small volume (a milliliter or less) and is enclosed within a compartment having a membrane means and one or more optical surfaces separating the aqueous fill solution from the sample chamber and from the optical system, respectively. The membrane means can permit rapid migration of alkali metal cations between the sample and the aqueous fill solutions so as to achieve an equilibrium or near-equilibrium. In some forms of the invention, however, an optical measurement is made at one or more fixed time points after the sample first contacts the membrane means, and either a non-equilibrium value or a slope of values is used. The membrane means should prevent the PCM from migrating out of the aqueous fill solution;

and, as described above, the inhibition of CPM migration can indirectly inhibit AFM migration. Some membrane means used may themselves provide selectivity as to what migrates into the aqueous fill solution (e.g., the membranes allows $K^+$ to enter, but not $Na^+$). It is preferred, however, to use membrane means which provide for the fastest possible cation migration; and, in most cases, such preference results in non-selective membrane means such as are used for dialysis (see Spectrum Medical Industries Catalog (1984/1985) and Encyclopedia of Chemical Technology, vol. 7, pp. 1–21 (Wiley & Sons 1963, H. F. Mark, et al., eds.) for a general discussion of suitable membranes for dialysis).

The optical surface(s) adjacent to the aqueous fill solution should permit excitation light to reach the AFM molecules (and especially those ion-paired with the ionophore/alkali metal cation complex) and for fluorescence to be detected from such AFMs. While either a conventional light source or a conventional light detector (as described further below) could in theory be placed at such surface(s), it is generally more convenient to conduct light to and from the aqueous fill solution by light paths such as optical fibers. The excitation light and fluorescent light may be conducted in opposite directions along the same light path using known techniques, or separate light paths may be used.

A preferred arrangement (as shown in FIGS. 1 and 3, described below) is to locate the enclosure for the aqueous fill solution adjacent to an end of a sample fiber optic (for both excitation and detection), with the ionophore (and especially the immobilized ionophore) disposed between the aqueous fill solution and the fiber optic. The membrane means can then be located on a different surface (e.g., the opposite surface) of the enclosure around the aqueous fill solution. In such case, AFM molecules complexed with ionophore/alkali metal cation complex are closest to the fiber optic. Such AFMs are prone to receive the greatest excitation light intensity and fluorescence from such AMFs are subjected to the least solution absorbance relative to AFMs complexed with CPMs. Nevertheless, as described above, it is preferred that the signal be modulated not merely by such geometrical effects, but also by the quenching or light shifting effects of the CPM on AFM molecules.

The excitation light used can be monochromatic (including light from a laser), can be filtered to provide a wavelength band or bands or can (in certain cases) be of broad spectrum (e.g., white light). Monochromatic light or light of a narrow band is preferred. The detection can (in certain instances) be of a narrow wavelength band or, with filters or the like, of a band of wavelengths. It is important to distinguish and detect fluorescent light apart from excitation light; such distinction can be established using particular angles, filters, detectors or other means as is well-known to the art. In the event that the CPM shifts the frequency of emitted light by AFM molecules complexed therewith (rather than simply quenches it), then it is preferred to use light paths, filters or detectors which distinguish AFM emissions of AFM molecules not ion-paired to CPM from AFM emissions of AFM molecules ion-paired to CPM.

FIG. 1 illustrates a first embodiment of a device in accordance with the present invention, as used in many of the Examples described below. A generally cylindrical fiber optic 10 extends vertically downward and is connected at its upper end to a monochromatic light source (schematically shown) and a detector (schematically shown). Two-sided adhesive, transparent tape 12 is stuck over the lower end of fiber optic 10; and silica particles 14, with adhering ionophore (e.g., valinomycin), are stuck on the outside (bottom) of tape 12. An elastomeric O-ring 16 surrounds the tape 12 and presses the tape 12 against the outside of fiber optic 10 so as to maintain tape 12 and particles 14 near the lower end of fiber optic 10.

The cylindrical fiber optic 10 with tape 12 is positional centrally within a glass tubing 18 of interior diameter larger than the exterior diameter of fiber optic 10. Glass tubing 18 extends downwardly a short distance beyond tape 12. The lower end of glass tubing 12 is covered with dialysis membrane 20 which is held in phase against the lower exterior of glass tubing 18 by a ring of flexible plastic (Tygon ®) tubing 22.

A fill solution 24 occupies the compartment around and below the lower portion of fiber optic 10, within the lower portion of glass tubing 18 and above dialysis membrane 20. The fill solution is therefore in direct contact with the particles 14 bearing ionophore and in indirect contact through dialysis membrane 20 with the sample compartment 26 (the boundaries of which are shown by the dashed lines), below dialysis membrane 20.

In the use of the device illustrated in FIG. 1, the fill solution contains cationic polymeric material (CPM, e.g., copper/PEI) and anionic fluorescent material (AFM, e.g., 9-1 ANS) as well as a buffer (e.g., Tris-HCl). Sample in compartment 26 contains a cation (e.g., $K^+$) which can migrate through dialysis membrane 20 into fill solution 24. The cation is sequestered by the ionophore (e.g., valinomycin) onto the particles 14 in an amount and at a rate functionally related to the concentration of such cation in sample compartment 26. The AFM migrates from the fill solution 24, where it has been ion-paired with the CPM, onto the particles 14, where it is ion-paired with the alkali metal cation/ionophore complex.

Excitation light is now transmitted down the fiber optic 10 onto the particles 14 and fill solution 24 (the tape 12 is transparent to the excitation light). To the extent that AFM has migrated to the particles 14, it absorbs such light and emits light, typically at a first and longer wavelength relative to the excitation light. This fluorescence of AFM molecules which have migrated to ionophore-complexed alkali metal cations can be transmitted back up fiber optic 10 and detected. It is preferred that at least such fluorescence from migrated AFMs be detected.

The AFMs that have remained in the fill solution 24, ion paired with the CPM, can also be detected; and in certain less preferred forms of the invention, only the fluorescence from AFM/CPM ion pairs are detected. To be detected, the fluorescence from AFM/CPM ion pairs must be distinguishable both from excitation light and from the fluorescence of migrated AFMs that are ion paired with ionophore/alkali metal cation complexes. Thus the emission from the AFM/CPM ion pairs should be at a second wavelength different from the first wavelength and from the excitation wavelength. For that purpose, either or both types of AFMs may be wavelength-shifted by their environments, or the AFM/CPM may represent an energy transferring pair of chromophores as described above.

In many forms of the invention, however, only the fluorescence of migrated AFMs is detected. In such case, the fluorescence of AFM ion-paired with CPM may be: (1) quenched by the CPM, (2) quenched by the solution between such ion pairs and the fiber optic 10, (3) of a wavelength filtered out (by the tape 12 or further up the fiber optic 10), (4) of a wavelength for which the detector is not responsive, (5) of a wavelength permitting removal or subtraction in the processing of the signal from the detector, or (6) some combination of factors (1) through (5).

FIG. 2 illustrates a second embodiment of a device in accordance with the present invention. As in the first embodiment, fiber optic 10 extends downwardly in a cylindrical shape. A cylindrical dialysis tubing 120 surrounds the lower end of fiber optic 10, with an inner diameter of dialysis tubing 120 larger than the outer diameter of fiber optic 10 by a fixed amount. The lower end of dialysis tubing 120, a fixed distance below the lower end of fiber optic 10, is plugged by impervious end seal 128. A fill solution 124 occupies the compartment within the lower portion of dialysis tubing 120 above end seal 128 and some portion of the lower exterior of fiber optic 10. Particles 114 bearing ionophore are suspended in fill solution 124.

The operation of the device of FIG. 2 is similar to that of the first embodiment illustrated in FIG. 1 with the following exceptions. Sample compartment 126 now surrounds dialysis tubing 120 and alkali metal cations migrate in through dialysis tubing 120 into fill solution 124. They are sequestered by ionophore on suspended particles 114, forming ionophore/alkali metal cation complexes, drawing AFMs away from CPMs in fill solution 124.

Upon excitation through fiber optic 10, both sets of AFMs are excited. The migrated AFMs can fluoresce, which fluorescence can pass through fill solution 124 to fiber optic 10, and then to the detector. Fluorescence from AFMs ion-paired with CPMs, if not quenched by the CPMs, can similarly pass through fill solution 124 to fiber optic 10 and then, if not filtered out, to the detector. If AFM/CPM represent an energy transfer pair, the CPM excited by AFM can fluoresce and produce a signal that, if not quenched or filtered out, can pass through fill solution 124 and fiber optic 10 to the detector. An appropriate analysis of one or more of these signals can be correlated with concentration of the selected alkali metal cation in sample compartment 126.

FIG. 3 illustrates a third embodiment of a device in accordance with the present invention. Elements 10, 18, 20, 22, 24, and 26 correspond in structure and function to similarly-numbered elements of the first embodiment of FIG. 1. Glass disc 214 is provided on the lower end of fiber optic 10. The lower edge 215 of glass disc 214 is coated with the ionophore (it is also possible to embed ionophore in glass disc 214 provided that glass disc 214 is permeable to fill solution 24 or at least to AFMs and to alkali metal cations).

The operation of the device of FIG. 3 is similar to that of FIG. 1 except that excitation light and both types of fluorescence must transverse glass disc 214 rather than tape 12. Glass disc 214 may also be used, if desired, to filter out the signal (e.g., fluorescence from AFM/CPM ion pairs) which one does not desire to detect.

In comparing the three embodiments, the principle difference relate to dialysis membrane 20 versus dialysis tubing 120 and to ionophore on particles 14 or disc 214 versus ionophore on suspended particles 114. Because dialysis membrane 120 offers a larger surface area and shorter migration path, it is expected that alkali metal cations in the sample compartment 126 of the second embodiment can come to equilibrium with the fill solution 124 more rapidly than can alkali metal cations in sample compartment 26. Such equilibration can be established both when a sample is introduced (before generating signal) and after it is replaced in the sample compartment by a flush solution (so that the fill solution can be returned to a rest condition of defined lower levels of alkali metal cations and high levels of AFM/CPM ion pairs). The disadvantage, however, of dialysis tubing 120 is that more AFM is likely to bleed through dialysis tubing 120 than through dialysis membrane 20. Depending upon the AFM and CPM chosen, and the desired lifetime of the fill solution 24 or 124 (which can be replaced periodically), one or the other of dialysis membrane 20 or dialysis tubing 120 may be preferred. Similarly, suspended particles 114 shorten the path for alkali metal cations to migrate, but lengthen the path for fluorescence from AFMs ion-paired with ionophore/alkali metal cation complexes. Which is chosen will depend upon the desired response time, the susceptibility of the fluorescence to interference and other factors. The choice between devices 20 and 120 and between ionophore supports 14, 114 and 214 are independent; thus, one may use suspended particles 114 within rubber tubing 18 capped with a dialysis membrane 20, or use disc 214 inside of dialysis tubing 120.

In the use of all three systems, the assemblies shown may be contacted (dipped in or having flow by) samples, then flush solution, then sample with little or no loss of AFM. Periodically, the fill solution can be removed or replenished, either by removing dialysis membrane 20 or plug 128 and immersing in fresh filling solution or by removing fiber optic 10, pouring out the old filling solution and pouring in fresh filling solution before replacing the fiber optic 10. The various other elements (especially dialysis elements 20 and 120 and ionophore-bearing elements 14, 114 and 214) can also be periodically replaced.

EXAMPLE 1

Detection of Sodium

Reagent—The reagent is sodium ionophore II (N,N'-"Dibenzyl-N,N'—diphenyl-1,2-phenylenedioxydiacetamide) purchased from Fluka. A known amount is dissolved in tetrahydrofuran and combined with a known amount of silica. The tetrahydrofuran is evaporated away leaving sodium ionophore II immobilized by adsorption on silica.

Filling Solution—The internal filling solution is 1.0 mL of 0.10 mM ANS, 0.10 mM Cu(II), 0.050 g/L polyethyleneimine, and 1.0 mM tris(hydroxymethyl)aminomethane buffer adjusted to pH 7.0.

Fiber Optic—The structure of FIG. 1 was assembled by placing a thin layer of the above-described sodium ionophore absorbed on silica gel on the top of a 3 mm diameter bifurcated fiber optic. The silica gel was held in place by covering with cellophane tape and holding it in place with an O-ring. The distance between the end of the fiber optic and the tape was 0.5 mm.

A piece of Spectrapor 2 dialysis membrane (from spectrum) was placed on the end of the glass tubing so as to define an aqueous fill space of 1.0 ml and provide a spacing between the cellophane tape and the dialysis membrane of 1.0 mm. The space was filled with 1.0 ml of the aqueous fill solution described above. The assembled device was stored in a solution of 5 ml Tris of pH 7.3.

Measurement of Sodium

Microliter amounts of standard sodium solutions or 500 microliters of human serum were injected into the sample cell (outside of the dialysis membrane). After stirring for three minutes, each of the standards or sample were determined for sodium by exciting the fiber optic at 380 mm and detecting at 460 mm.

Values were taken here for ANS concentrations of $5\times10^{-6}$, $1\times10^{-5}$, $5\times10^{-5}$, $1\times10^{-4}$ and $5\times10^{-4}$ molar (respectively, 5, 10, 50, 100 and 500 micromolar):

| | Relative Fluorescence Intensity | | | | |
|---|---|---|---|---|---|
| | uM ANS | | | | |
| mM Na+ | 5 | 10 | 50 | 100 | 500 |
| 0 | 0 | 0 | 0 | 0 | 0 |
| 20 | 4 | 13 | 16 | 4 | 33 |
| 40 | 7 | 20 | 32 | 40 | 57 |
| 60 | 8.5 | 26 | 44 | 57 | 74 |
| 80 | 10 | 31 | 52 | 68 | 86 |
| 100 | 11.5 | 35 | 56 | 77 | 92 |
| 120 | 13 | 38 | 62 | 83 | 96 |
| 140 | 14.5 | 42 | 67 | 89 | 98 |
| 160 | 15.5 | 46 | 71 | 93 | 100 |
| 180 | 16 | 49 | 74 | 96 | 100 |
| 200 | 17.5 | 52 | 76 | 97 | 100 |

Such data shows that different ANS levels give linear or near-linear responses over a range of Na+ values: e.g., the 5 uM ANS curve is reasonably linear below 200 mM Na+ while the 50 uM ANS curve is reasonably linear between 0 and 80 mM Na+.

EXAMPLE 2

Effects of pH on Response to Sodium

Using a reagent phase consisting of 0.10 mmol sodium ionophore II/gram of silica substrate and 1.0 mL of internal filling solution containing 0.1 mM ANS, 0.10 mM Cu(II) and 0.050 g/L polyethylenimine, response to 20.0 mM sodium was measured using buffers to adjust pH

| pH | Relative Fluorescence Intensity |
|---|---|
| 3.0 | 30 |
| 4.0 | 37 |
| 5.0 | 43 |
| 5.8 | 50 |
| 7.0 | 71 |
| 8.0 | 93 |
| 9.0 | 103 |
| 10.0 | 103 |
| 11.0 | 107 |

Such data shows that sodium can be measured over a wide range of pH values and that response varies with pH but not to a high degree.

EXAMPLE 3

Effect of Temperature on Response to Sodium

Using the same reagent phase as in Example 2 at pH 7 and a solution of 20 mM sodium, the relative fluorescence intensities was measured as a function of temperature.

| Temperature (C.) | Relative Fluorescence Intensity |
|---|---|
| 20 | 73 |
| 30 | 56 |
| 40 | 39 |
| 50 | 22 |
| 60 | 14 |

Such data shows how temperature affects response to sodium.

EXAMPLE 4

Effects of Amounts of Immobilized Ionophore

Using a reagent phase consisting of sodium ionophore II immobilized by adsorption on silica and 1.0 mL of 0.10 mM ANS, 0.10 mM Cu(II), 0.050 g/L polyethyleneimine and 0.0010M tris(Hydroxymethyl)aminomethane buffer at pH 7.0, relative fluorescence intensity was measured as a function of the amount of sodium ionophore II per gram of silica.

| mmol ionophore/gram silica | Relative fluorescence |
|---|---|
| 0.010 | 5 |
| 0.050 | 20 |
| 0.070 | 33 |
| 0.10 | 44 |
| 0.20 | 57 |
| 0.30 | 70 |
| 0.40 | 79 |

These data show how the magnitude of the response can be increased by using more ionophore.

EXAMPLE 5

Effect of added interferants

Using a reagent phase consisting of 0.10 mmol of sodium ionophore II per g of silica and an internal filling solution as described above under Example 1, response to 20 mM sodium ion was compared in the absence and presence of other added species.

| Added species | Concentration | Relative fluorescence intensity |
|---|---|---|
| None | | 100 |
| potassium (I) | 5 mM | 120 |
| calcium (II) | 5 mM | 115 |
| magnesium (II) | 5 mM | 103 |
| chloride | 200 mM | 100 |
| bicarbonate | 120 mM | 100 |
| phosphate | 100 mM | 102 |
| sulfate | 100 mM | 100 |
| bovine serum albumin | 2% | |

These data show that the sensor is selective for sodium in the presence of other ions likely to be present in serum.

EXAMPLE 6

Response to potassium

Reagent

The reagent is 0.10 mmol dibenzo-18-crown-6 immobilized by adsorption on silica.

Internal filling solution

The internal filling solution is the same in Example 1. Response was measured as a function of potassium concentration.

| Concentration (mM) | Relative fluorescence |
| --- | --- |
| 2 | 8.5 |
| 4 | 17 |
| 6 | 25 |
| 8 | 34 |
| 10 | 43 |
| 12 | 51 |
| 14 | 59 |
| 16 | 67 |
| 18 | 73 |
| 20 | 79 |

These data illustrate the use of another ionophore and demonstrate that the method is general for neutral cation-binding ionophores.

EXAMPLE 7

Screening of anionic fluorophors

Anionic fluorophores other than 8, 1-ANS were tested to see whether (a) their fluorescence was quenched in the presence of CU(II), and polytheyleneimine and (b) whether the addition of immobilized ionophore led to the formation of a fluorescent ion pair.

| Fluorophore | Quenched (?) | Fluorescent Ion Pair (?) |
| --- | --- | --- |
| 2,5-ANS | Yes | Yes |
| Nuclear Fast Red | Yes | Yes |
| Fluorescein | No | |
| Eosin Y | Yes | Yes (below pH 6 only) |
| pyrenebutyric acid | No | No |
| aminopyrenesulfonic acid | Yes | No |

These data demonstrate that the method can be generalized to other anionic fluorophors (although not all anionic fluorophors work).

EXAMPLE 8

Measurement of Sodium in Serum

Using the same reagent and internal filling solution as in Example 1, the concentration of sodium was measured in six serum samples.

| Sample # | Conc. |
| --- | --- |
| 1 | 132.3, 141.3 |
| 2 | 165.9, 168.6, 161.4 |
| 3 | 134.5, 132.2 |
| 4 | 143.5, 146.1 |
| 5 | 145.7, 143.5 |
| 6 | 148.5, 152.5, 154.7, 152.5, 156.9 |

These data demonstrate that the method can be used to yield reproducible results in a serum matrix.

EXAMPLE 9

Satisfactory results were also obtained employing the following ionophores:

Valinomycin (for potassium), dibenzo-18-crown-6 (for potassium), dicyclohexyl-18-crown-6 (for potassium), 18-crown-6 (for potassium), sodium ionophore 1 (from Fluka), and sodium ionophore 2 (from Fluka).

We claim:

1. A method for determining the concentration of a selected alkali metal cation in an aqueous sample which comprises the steps of:
    (a) providing an aqueous fill solution containing a dissolved polymeric cationic material and a dissolved fluorescent anionic material, wherein said polymeric cationic material is initially present in said fill solution as an ion paired complex with said fluorescent anionic material;
    (b) providing in contact with the fill solution an ionophore selective for the selected alkali metal cation, said fluorescent anionic material being such that it is also capable of complexing in an ion pairing relationship with a complex of said ionophore and the selected alkali metal cation, the fluorescence of said fluorescent anionic material when it is complexed with said polymeric cationic material being different from the fluorescence of said fluorescent anionic material when it is complexed with a complex of said ionophore and the selected alkali metal cation;
    (c) contacting the aqueous fill solution with an aqueous sample through a membrane which is permeable to alkali metal cations but impermeable to said polymeric cationic material; and
    (d) determining the concentration of the selected alkali metal cation in said aqueous sample by detecting fluorescence from (1) fluorescent anionic material which has migrated from being complexed with said polymeric cationic material to being complexed with a complex of said ionophore and the seleced alkali metal cation, (2) fluorescent anionic material which has remained complexed with said polymeric cationic material, or (3) fluorescent anionic material as defined in both (1) and (2).

2. The method of claim 1 wherein the membrane is permeable to the fluorescent anionic material when it is not complexed, but is impermeable to the fluorescent anionic material complexed with the polymeric cationic material.

3. The method of claim 1 wherein the selected alkali metal is $Na^+$.

4. The method of claim 1 wherein the selected alkali metal cation is $K^+$ and the ionophore has a selectivity for $K+$ relative to $Na+$ of at most about $10^{-3}$.

5. The method of claim 1 wherein the ionophore is immobilized in or on a solid phase.

6. The method of claim 1 wherein the ionophore is in an organic phase adjacent the fill solution.

7. The method of claim 1 wherein the fluorescent anionic material is substantially water-insoluble when it is not complexed, but is solublized in the aqueous fill solution by being complexed with the polymeric cationic material.

8. The method of claim 7 wherein the concentration of the fluorescent anionic material in the fill solution is in excess of the solubility limits of the fluorescent anionic material in water when it is not complexed.

9. The method of claim 1 wherein the fluorescence of the fluorescent anionic material is quenched by the cationic polymeric material when it is complexed therewith.

10. The method of claim 9 wherein the detecting step comprises detecting unqunched fluorescent emission of fluorescent anionic material which has migrated from being complexed with said polymeric cationic material to being complexed with a complex of said ionophore and the seleced alkali metal cation.

11. The method of claim 9 wherein the detecting step comprises exciting the anionic fluorescent material with excitation light which does not excite the cationic polymeric material and detecting emission from cationic polymeric material which is excited by emission from fluorescent anionic material which has remained complexed therewith.

12. The method of claim 1 wherein the polymeric cationic material comprises polyethyleneimine.

13. The method of claim 12 wherein the polymeric cationic material further comprises a transition metal.

14. The method of claim 13 wherein the transition metal is copper.

15. The method of claim 12 wherein the polymeric cationic material further comprises a cationic dye.

16. The method of claim 15 wherein the cationic dye is rhodamine.

17. An article of manufacture for determining the concentration of a selected alkali metal cation in an aqueous sample which article comprises:
(a) a container filled with an aqueous fill solution containing a dissolved polymeric cationic material and a dissolved fluorescent anionic material, wherein said polymeric cationic material is present in said fill solution as an ion paired complex with said fluorescent anionic material;
(b) an ionophore selective for the selected alkali metal cation in contact with the aqueous fill solution, said fluorescent anionic material being such that it is also capable of complexing in an ion pairing relationship with a complex of said ionophore and the selected alkali metal cation, the fluorescence of said fluorescent anionic material when it is complexed with said polymeric cationic material being different from the fluorescence of said fluorescent anionic material when it is complexed with a complex of said ionophore and the selected alkali metal cation;
(c) membrane means forming a wall of said container and being in contact with the aqueous fill solution, said membrane means being permeable to alkali metal cations but impermeable to said polymeric cationic material;
(d) excitation means for exciting the fluorescent anionic material; and
(e) detection means for detecting fluorescence either from fluorescent anionic material which has migrated from being complexed with said polymeric cationic material to being complexed with a complex of said ionophore and the selected alkali metal cation or fluorescent anionic material which has remained complexed with said polymeric cationic material.

18. The article of claim 17 wherein the excitation means comprises a monochromator and the detection means comprises a fiber optic.

19. the article of claim 17 wherein the membrane means is permeable to the fluorescent anionic material when it is not complexed, but is impermeable to the fluorescent anionic material complexed with the polymeric cationic material.

20. The article of claim 17 wherein the selected alkali metal is $Na^+$.

21. The article of claim 17 wherein the ionophore is immobilized in or on solid phase.

22. The article of claim 17 wherein the polymeric cationic material is such that it quenches the fluorescence of the fluorescent anionic material when it is complexed therewith.

23. The article of claim 22 wherein the detection means is such that it detects unquenched fluorescent emission of fluorescent anionic material which has migrated from being complexed with said polymeric cationic material to being complexed with a complex of said ionophore and the selected alkali metal cation.

24. The article of claim 17 wherein the polymeric cationic material comprises polyethyleneimine.

25. The article of claim 24 wherein the polymeric cationic material further comprises a transition metal.

26. The article of claim 25 wherein the transition metal is copper.

* * * * *